(12) United States Patent
Shaw et al.

(10) Patent No.: US 10,342,929 B2
(45) Date of Patent: Jul. 9, 2019

(54) FRONTAL ATTACHMENT DEVICE FOR SYRINGE WITH ROTATIONALLY ACTIVATED RETRACTABLE NEEDLE

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 657 days.

(21) Appl. No.: 15/090,343

(22) Filed: Apr. 4, 2016

(65) Prior Publication Data

US 2016/0317756 A1 Nov. 3, 2016

Related U.S. Application Data

(63) Continuation of application No. 14/091,113, filed on Nov. 26, 2013, now Pat. No. 9,302,055.

(60) Provisional application No. 61/737,263, filed on Dec. 14, 2012.

(51) Int. Cl.
*A61M 5/32* (2006.01)

(52) U.S. Cl.
CPC ........ *A61M 5/3232* (2013.01); *A61M 5/3276* (2013.01); *A61M 5/321* (2013.01); *A61M 2005/3224* (2013.01); *A61M 2005/3227* (2013.01)

(58) Field of Classification Search
CPC .. A61M 5/3205; A61M 5/322; A61M 5/3232; A61M 5/3276; A61M 2005/3206; A61M 2005/3208; A61M 2005/3224; A61M 2005/3227
See application file for complete search history.

(56) References Cited

U.S. PATENT DOCUMENTS

| 4,466,446 A | | 8/1984 | Baidwan et al. |
| 4,747,831 A | | 5/1988 | Kulli |
| 4,813,426 A | * | 3/1989 | Haber ................. A61M 5/322 600/576 |
| 4,863,426 A | | 3/1989 | Haber et al. |
| 4,941,883 A | | 7/1990 | Venturini |
| 4,973,316 A | | 11/1990 | Dysarz |
| 5,163,916 A | * | 11/1992 | Sunderland ........... A61M 5/002 604/110 |

(Continued)

FOREIGN PATENT DOCUMENTS

| EP | 0479303 | 8/1992 |
| EP | 1161962 | 12/2001 |
| JP | H10179738 | 7/1998 |

*Primary Examiner* — Andrew M Gilbert
(74) *Attorney, Agent, or Firm* — Ross Barnes LLP; Monty L. Ross

(57) ABSTRACT

A medical device attachable to the front of a conventional syringe and having a hub assembly selectively attachable to the syringe, a nose projecting forwardly from the hub assembly, a rearwardly biased needle retraction mechanism seated inside the nose, a retractable needle projecting forwardly of the nose, and a fluid flow path from the fluid chamber through the hub assembly, nose, needle retraction assembly and needle, wherein the needle is retracted into the nose and a retraction tube external to the syringe by rotating the syringe relative to the nose.

33 Claims, 10 Drawing Sheets

(56) References Cited

U.S. PATENT DOCUMENTS

| | | |
|---|---|---|
| 5,263,942 A | 11/1993 | Smedley et al. |
| 5,298,023 A | 3/1994 | Haber et al. |
| 5,354,284 A * | 10/1994 | Haber .................... A61M 5/19 604/191 |
| 5,370,628 A | 12/1994 | Allison et al. |
| 5,395,337 A | 3/1995 | Clemens et al. |
| 5,423,758 A | 6/1995 | Shaw |
| 5,445,618 A | 8/1995 | Adobbati |
| 5,503,010 A | 4/1996 | Yamanaka |
| 5,573,510 A | 12/1996 | Isaacson |
| 5,685,863 A | 11/1997 | Botich et al. |
| 5,704,920 A | 1/1998 | Gyure |
| 5,728,073 A | 3/1998 | Whisson |
| 5,779,679 A | 7/1998 | Shaw |
| 5,795,339 A | 8/1998 | Erskine |
| 5,957,887 A | 9/1999 | Osterlind et al. |
| 5,964,731 A | 10/1999 | Kovelman |
| 6,039,713 A | 3/2000 | Botich et al. |
| 6,063,040 A | 5/2000 | Owen et al. |
| 6,210,371 B1 | 4/2001 | Shaw |
| 6,277,102 B1 | 8/2001 | Carilli |
| 6,468,250 B2 | 10/2002 | Yang |
| 6,808,512 B1 | 10/2004 | Lin et al. |
| 6,974,423 B2 | 12/2005 | Zurcher |
| 7,351,224 B1 | 4/2008 | Shaw |
| 8,292,852 B2 | 10/2012 | Mulholland |
| 8,343,094 B2 | 1/2013 | Shaw |
| 8,469,927 B2 | 6/2013 | Shaw et al. |
| 8,496,600 B2 | 7/2013 | Shaw et al. |
| 8,500,690 B2 | 8/2013 | Crawford |
| 9,138,545 B2 * | 9/2015 | Shaw .................... A61M 5/3232 |
| 9,302,055 B2 * | 4/2016 | Shaw .................... A61M 5/3232 |
| 2001/0021827 A1 | 9/2001 | Ferguson et al. |
| 2002/0068907 A1 * | 6/2002 | Dysarz ................ A61M 5/3232 604/191 |
| 2002/0082560 A1 * | 6/2002 | Yang .................... A61M 5/3232 604/181 |
| 2003/0078540 A1 | 4/2003 | Saulenas et al. |
| 2003/0181871 A1 | 9/2003 | Wilkinson et al. |
| 2003/0236504 A1 | 12/2003 | Chen |
| 2004/0015135 A1 | 1/2004 | Wilkinson |
| 2004/0019329 A1 | 1/2004 | Erskine |
| 2004/0204688 A1 * | 10/2004 | Lin .................... A61M 5/3232 604/192 |
| 2005/0004524 A1 | 1/2005 | Newby et al. |
| 2005/0288607 A1 | 12/2005 | Konrad |
| 2006/0155244 A1 * | 7/2006 | Popov ................ A61M 25/0625 604/162 |
| 2006/0189934 A1 | 8/2006 | Kuracina et al. |
| 2006/0235354 A1 | 10/2006 | Kaal et al. |
| 2007/0260189 A1 | 11/2007 | Shaw et al. |
| 2008/0132851 A1 | 6/2008 | Shaw et al. |
| 2008/0132854 A1 | 6/2008 | Sharp |
| 2008/0287881 A1 | 11/2008 | Kiehne |
| 2008/0319345 A1 | 12/2008 | Swenson |
| 2009/0198196 A1 | 8/2009 | West et al. |
| 2009/0306601 A1 * | 12/2009 | Shaw .................... A61M 5/158 604/177 |
| 2010/0000040 A1 | 1/2010 | Shaw et al. |
| 2010/0003067 A1 | 1/2010 | Shaw et al. |
| 2010/0217207 A1 * | 8/2010 | Shams ................ A61M 5/3232 604/240 |
| 2010/0241029 A1 | 9/2010 | Mahurkar |
| 2010/0286604 A1 | 11/2010 | Shaw |
| 2010/0317999 A1 | 12/2010 | Shaw et al. |
| 2011/0264037 A1 | 10/2011 | Foshee et al. |
| 2012/0022464 A1 | 1/2012 | Zivkovic et al. |
| 2012/0071790 A1 | 3/2012 | Mahurkar |
| 2012/0078225 A1 * | 3/2012 | Zivkovic ............ A61M 5/3213 604/506 |
| 2012/0226232 A1 | 9/2012 | Shaw et al. |
| 2012/0259243 A1 | 10/2012 | Shaw et al. |
| 2012/0316466 A1 | 12/2012 | Crawford et al. |
| 2014/0012206 A1 | 1/2014 | Shaw et al. |

\* cited by examiner

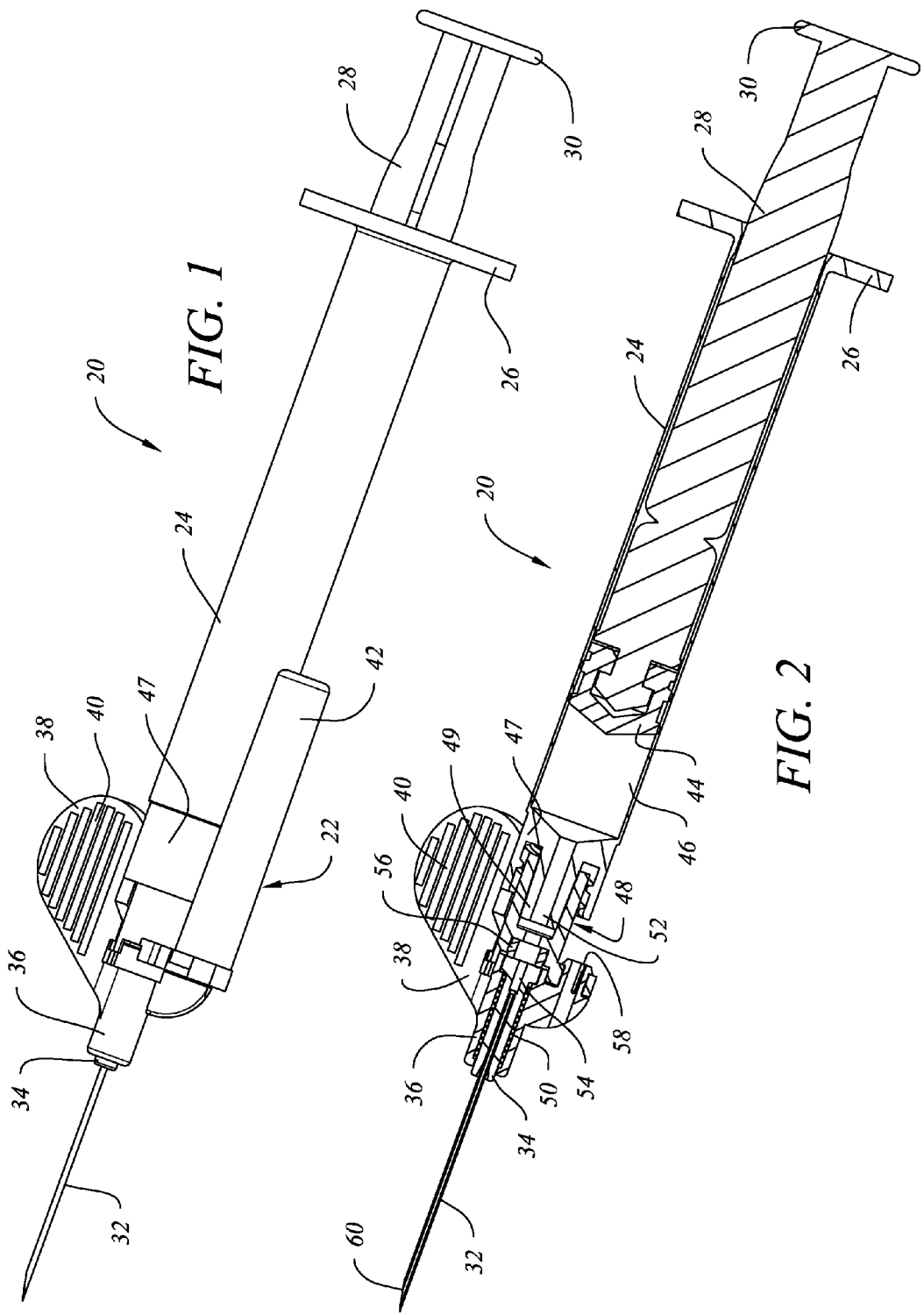

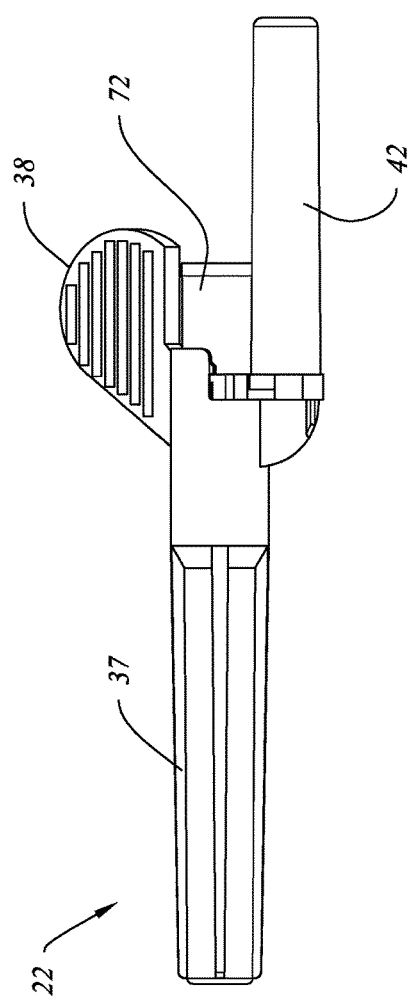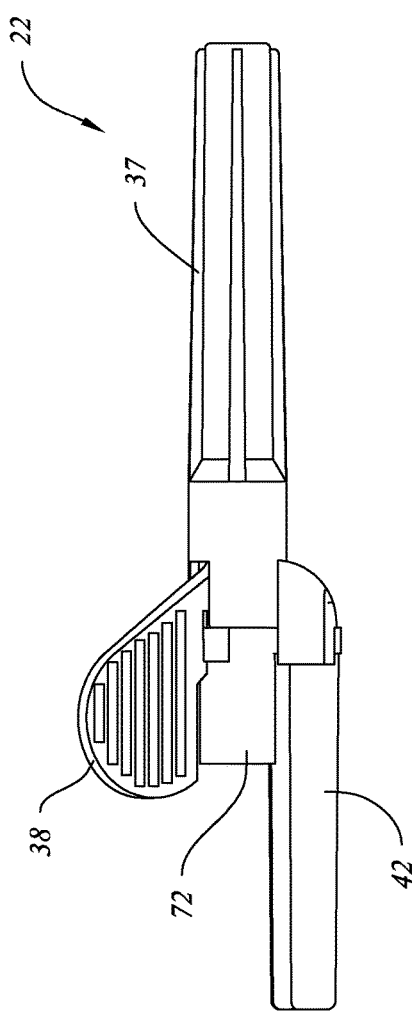

FRONTAL ATTACHMENT DEVICE FOR SYRINGE WITH ROTATIONALLY ACTIVATED RETRACTABLE NEEDLE

CROSS-REFERENCE TO RELATED APPLICATIONS

This application is a continuation of U.S. application Ser. No. 14/091,113 filed Nov. 26, 2013, now U.S. Pat. No. 9,302,055, issued Apr. 5, 2016, which claims the benefit under 35 U.S.C. 119(e) of the earlier filing date of U.S. Provisional Patent Application No. 61/737,263 filed Dec. 14, 2012.

BACKGROUND OF THE INVENTION

1. Field of the Invention

This invention relates to the use of conventional syringes in combination with a newly disclosed frontal attachment having a retractable needle. The invention relates more particularly to a medical device comprising in combination a needle, nose and hub assembly attachable to a conventional syringe preferably having a forwardly facing luer lock connector. The subject device has a needle retraction mechanism that is activated by rotating the syringe barrel relative to the nose of the device to retract the needle from a patient and propel it into the nose and a retraction tube that is part of the hub assembly.

2. Description of Related Art

Conventional syringes comprising a generally cylindrical barrel, a fixed needle projecting forwardly from the barrel, and a plunger slidably disposed inside the barrel through an opening in the rear of the barrel are well known. More recently, syringes have been made with a luer connector on the front of the barrel to which a needle hub is attachable to allow needles of different gauges or sizes to be used with a commonly configured barrel.

Even more recently, in an effort to control the spread of blood-borne pathogens and the incidence of contamination by contact with either exposed needles or bodily fluids, syringes having fixed or changeable needles have been designed to embody various "safety" elements. Such "safety" elements should desirably include a retractable needle, but many products marketed as having "safety" elements include, for example, covers or guards that are manually operated by medical personnel administering an injection to shield or cover the needle tip following removal of the needle from a patient.

Some previously disclosed needle retraction systems without changeable needles are activated either manually or automatically by application of a force upon completion of an injection to force the needle and needle tip back inside a retraction chamber. The only known syringe having a changeable, retractable needle does not have a conventional luer lock connection, and the retraction mechanism is activated by the application of a forwardly directed force to the plunger handle following removal of the needle from a patient, thereby exposing the needle and also exposing the user to the risk of needle-stick injury.

U.S. Pub. No. 2006/0155244 to Popov discloses a venipuncture device that rotates a port unit following needle retraction. The retraction chamber is disposed inside the medical device, is not part of the frontal attachment and remains stable while the port unit is moved rotationally relative to the retraction chamber following needle retraction. The frontal attachment disclosed there cannot be used with a generic luer lock syringe.

Although many advancements in syringe technology have been made in recent years, a frontal attachment device is needed that can be used with a standard syringe having a conventional luer lock connector, that offers the advantages of a changeable needle in combination with the advantages of a retractable needle providing sufficient retraction force to retract the needle while inserted into a patient, and that can be activated by the application of a rotational force to the syringe barrel while stabilizing the nose without applying a forwardly directed force to the plunger or the needle.

SUMMARY OF THE INVENTION

A medical device is disclosed that comprises a hub assembly selectively attachable to the front of a conventional syringe, a nose projecting forwardly from the hub assembly, a rearwardly biased needle retraction mechanism seated inside the nose, a retractable needle projecting forwardly of the nose, and a fluid flow path from the fluid chamber through the hub assembly, nose, needle retraction mechanism and needle, wherein the needle is retracted following use into the nose and a retraction tube external to the syringe by rotating the syringe relative to the nose. As used throughout this disclosure, the terms "attachable," "detachable" and "changeable" are generally used to characterize frontal attachments, such as needles or needle/hub combinations, that are selectively attachable to, detachable from, or otherwise changeable in relation to a syringe for purposes such as, without limitation, selecting a particular gauge needle for a particular clinical use.

A medical device as disclosed here can be configured to be attachable to the front of a conventional syringe having a luer lock connector. If desired, a medical device as disclosed here can also be made with a snap-on or other attachment mechanism instead of a conventional luer lock connector provided that the syringe with which it is used is cooperatively configured. A medical device as disclosed here desirably comprises a needle that is retractable, and retraction is activated by applying rotational rather than axial force to the syringe barrel. A satisfactory medical device as disclosed here desirably has sufficient retraction force to retract a needle that is still inserted into a patient's body and thereby prevents exposure of the contaminated needle to others. A medical device as disclosed here desirably utilizes a retraction tube that is not embodied in the syringe or plunger handle, and is instead part of the attachable hub assembly.

A satisfactory hub assembly for use in the invention as disclosed here comprises a hub disposed forwardly of the plunger, a retraction tube laterally spaced apart from the hub, and a frame member interconnecting the hub and the retraction tube in substantially fixed, laterally spaced-apart relation to each other. A medical device made in accordance with the invention desirably further comprises a nose projecting forwardly from the hub and is attached to the frame so as to permit the hub assembly to move laterally in relation to the nose between a first position axially aligned with the hub and a second position axially aligned with the retraction tube. A rearwardly biased needle retraction mechanism comprising a needle holder and retraction spring is desirably seated inside the nose; and a retractable needle projects forwardly of the nose. A fluid flow path is thereby provided from the fluid chamber of a syringe through the hub, nose, needle retraction assembly and needle; and an annular fluid seal is desirably disposed around a portion of the fluid flow path between the hub and the nose.

Following an injection using a syringe provided with the medical device disclosed here, a clinician administering the injection desirably grasps a stabilizer tab provided at the nose of the device with the thumb and finger or fingers of one hand to stabilize the body and nose, and with the other hand, rotates the syringe barrel in a clockwise direction (the same direction in which the barrel is rotated during attachment of the syringe to the device prior to use). As the body and nose are stabilized, the syringe barrel and the attached hub assembly are rotated relative to the nose, which first causes the hub to slide laterally out of coaxial alignment with the head of the needle holder. As the hub slides out of engagement with the rearwardly biased needle holder, preferably in a curvilinear arc, a portion of the frame member disposed between and connecting the hub to the laterally spaced-apart retraction tube comes into abutting engagement with the needle holder to continue holding the retraction spring in its compressed position. The needle holder remains rearwardly biased until such time as a forwardly facing opening into the retraction tube sufficiently approaches coaxial alignment with the needle holder to allow the compressed retraction spring to propel the needle holder rearwardly into the retraction tube. As this occurs, the needle holder also carries the attached needle rearwardly to a fully retracted position where the needle is released from the patient and the needle tip no longer projects forwardly from the nose.

In this way, the medical device disclosed here is configured to convert rotational motion of the syringe to curvilinear translational realignment of the nose and the needle holder from coaxial alignment with the hub to coaxial alignment with the retraction tube.

BRIEF DESCRIPTION OF THE DRAWINGS

The apparatus of the invention is further described and explained in relation to the following drawings wherein:

FIG. 1 is a side elevation view of one embodiment of a syringe having selectively attached to its front end one embodiment of a medical device comprising in combination a nose, a needle or cannula projecting forwardly of the nose, a needle retraction mechanism seated inside the nose, and a hub assembly;

FIG. 2 is a cross-sectional view of the apparatus of FIG. 1 taken along line 2-2 of FIG. 9;

FIGS. 15-17 are right, left side and front elevation views, respectively, of the medical device of FIG. 1, with a needle cover installed prior to use.

Like reference numerals are used to describe like features in all Figures of the drawings.

DESCRIPTION OF THE PREFERRED EMBODIMENTS

Figure 3:
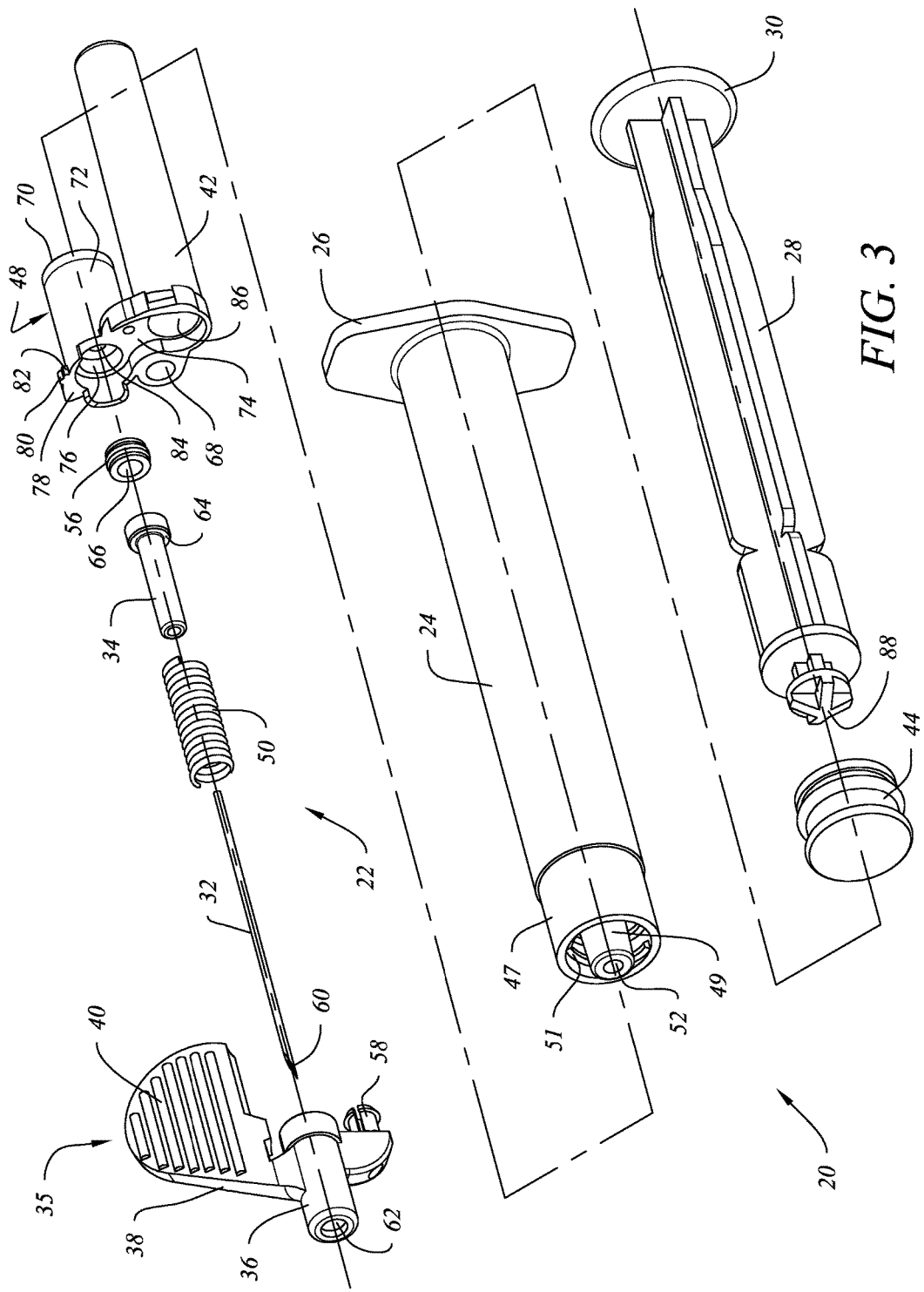
FIG. 3 is an exploded perspective view of the apparatus of FIG. 1.

FIGS. 1 and 2 depict an assembled combination 20 of syringe barrel 24, having a luer lock connector 47, 49 disposed at the front end and a plunger handle 28 with plunger seal 44 slidably engaging the inside wall of syringe barrel 24, and a satisfactory medical device 22 of the invention having a hub assembly 48 that is attached to luer lock connector 47, 49 so as to establish fluid communication between fluid chamber 46 of syringe barrel 24 and needle 32. Plunger handle 28 extends rearwardly from an opening in the back of syringe barrel 24 and is positioned relative to syringe barrel 24 as it could be prior to the injection of a fluid disposed inside fluid chamber 46 into a patient if tip 60 of needle 32 were inserted into the patient, recognizing that the position of plunger seal 44 relative to barrel 24 will depend upon the amount of fluid that is drawn into fluid chamber 46. The injection force is applied to a fluid disposed inside fluid chamber 46 through plunger handle 28 by depressing thumb cap 30 of plunger handle 28 while stabilizing syringe barrel 24 by applying oppositely directed finger force to the forwardly facing surfaces of outwardly projecting flanges 26.

Figure 4:
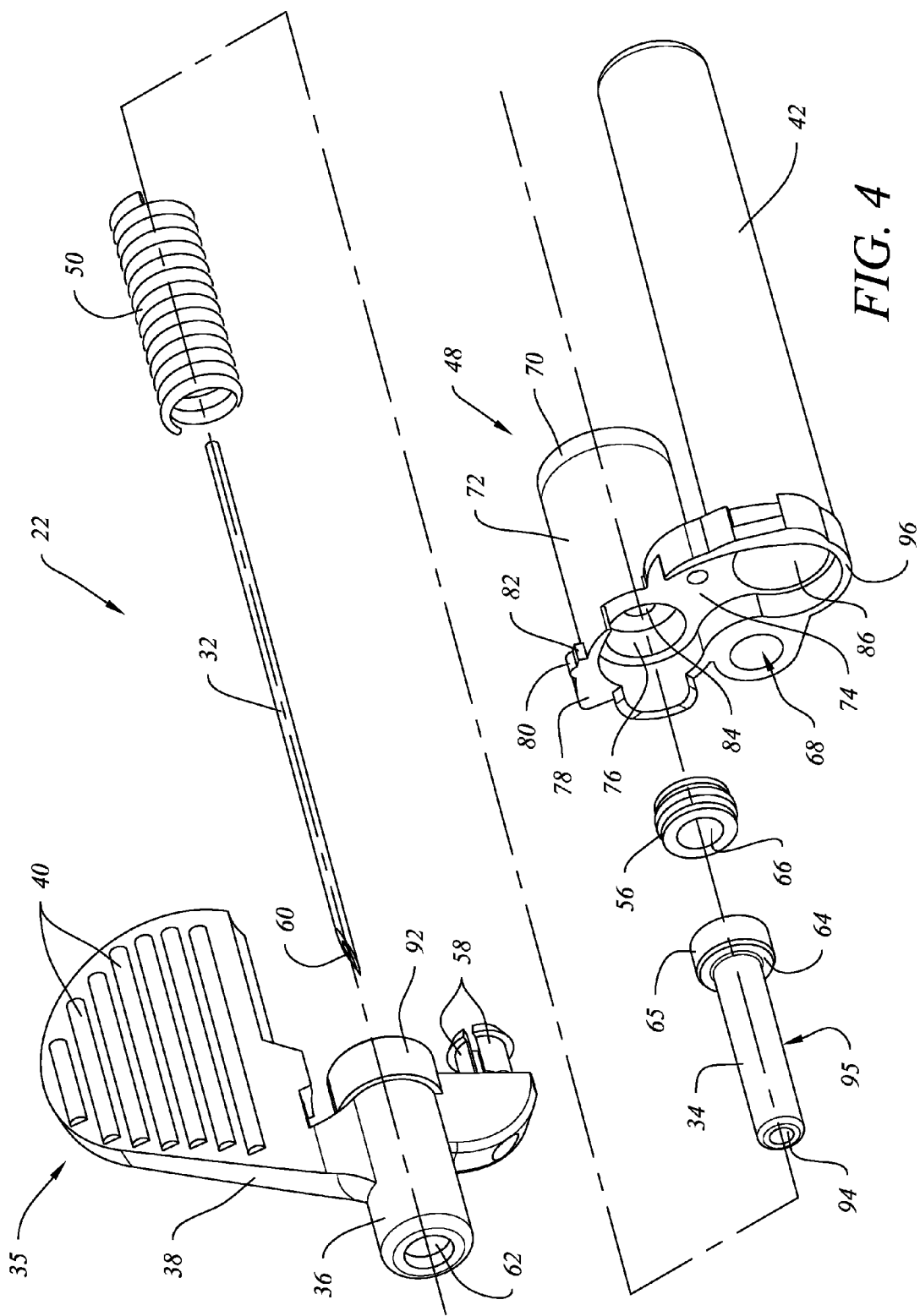
FIG. 4 is an enlarged detail view of the attachable medical device of FIG. 1.

During or following the injection, a clinician administering the injection can grasp the textured surfaces of outwardly projecting stabilizer tab 38 of medical device 22 to stabilize medical device 22 and rotate syringe barrel 24, preferably in a clockwise direction (as viewed from the back of assembled combination 20), relative to stabilizer tab 38 of nose 35 (best seen in FIG. 4). Although medical device 22 of the invention can be made so as to permit rotation of syringe barrel 24 in either a clockwise or counter-clockwise direction relative to stabilizer tab 38 of nose 35 to achieve needle retraction, one or more mechanical barriers to counter-clockwise rotation of syringe barrel 24 are desirably provided to avoid accidentally unthreading luer lock connector 47, 49 of syringe barrel 20 from nose 35.

Satisfactory structural elements for use in combination 20 and in medical device 22 of the invention are further described and explained in relation to FIGS. 1-4. Medical device 22 as shown comprises nose 35, a retraction mechanism further comprising a needle holder 95 (FIG. 4) and a compressed retraction spring 50 seated inside nose 35, and hub assembly 48 comprising hub 72, frame member 74, retraction tube 42 further comprising retraction cavity 86, and an annular fluid seal such as fluid seal 56 that is desirably disposed between nose 35 and hub 72, preferably inside a recess 76 in the forwardly facing portion of hub 72. A plurality of radially projecting locking wedges 70, diametrically opposed as shown, or other similarly effective engagement elements are provided at the rear of hub 72 to facilitate locking engagement with locking luer connector 47, 49 of syringe barrel 24.

Referring to FIG. 4, needle holder 95 as shown comprises elongated cylindrical shaft portion 34, a larger diameter head 65, which is seated against an annular shoulder inside substantially cylindrical body 36 of nose when the retraction mechanism is seated inside nose 35 prior to attaching nose 35 to hub assembly 48 as further described below. Prior to seating needle holder 95 inside body 36 of nose 35, retraction spring 50 is desirably compressed (spring 50 is shown compressed in FIGS. 2-4 and relaxed in FIG. 8) between an annular nose 39 near the front of body 36 (best seen in FIG. 8) and annular shoulder 64 (FIG. 4) on the forwardly facing surface of head 65 of needle holder 95. The length of cylindrical shaft portion 34 of needle holder 95 is desirably such that the forwardly extending end of shaft portion 34 will project slightly beyond the front of body 36 as seen in FIG. 1.

As shown, nose 35 further comprises substantially cylindrical body 36 having a rearwardly facing collar 92, and an outwardly projecting stabilizer tab 38 with textured gripping elements 40. Body 36 of nose 35 desirably further comprises an attachment tab 100 (FIG. 6) projecting radially outward below the longitudinal axis through interior cavity 62 that has a rearwardly projecting, split cylindrical boss 58 configured to snap into a cooperatively aligned orifice 68 in frame member 74 of hub assembly 48. Nose 35 is thereby rotatably attached to hub assembly 48 with the axis of rotation being offset from the longitudinal axes through hub 72 and retraction tube 42 so as to define an arc through which hub assembly 48 can be moved translationally from a first position characterized by coaxial alignment of hub 72 with body 36 to a second position characterized by coaxial alignment of retraction tube 42 with body 36 to initiate retraction following injection. Although the structural elements as disclosed are satisfactory for rotatably mounting nose 35 in relation to hub assembly 48, it will be appreciated by those of ordinary skill in the art upon reading this disclosure that other structural elements and configurations can be substituted for those particularly disclosed here to achieve the same functionality within the scope of the invention. Broadly stated, such functionality comprises rotating a syringe barrel following injection to move the barrel translationally relative to a nose portion comprising a retraction mechanism to initiate retraction of a needle from a patient into a cavity inside a retraction tube so that the tip of the needle no longer projects forwardly of the barrel.

As shown in FIG. 3, a syringe suitable for use with medical device 22 of the invention can comprise barrel 24 with radially projecting flanges 26 disposed along the rear portion of barrel 24, an engagement structure such as luer lock connector 47, 49 attachable to hub assembly 48, plunger seal 44 attached to mounting boss 88 of plunger handle 28, and a thumb cap 30 to facilitate the application of a forwardly directed force to plunger handle 28 relative to barrel 24 during injection. As shown, tapered luer member 49 comprising a substantially cylindrical bore 51 cooperates with annular collar 47 having internal threads 51 disposed in spaced-apart relation to tapered luer member 49 to form luer lock connector 47, 49 that is engageable with locking wedges 70 of hub 72 to provide a fluid-tight seal between hub 72 and syringe barrel 24. When combination 20 is assembled as shown in FIG. 1, a continuous fluid flow path is formed from fluid chamber 46 (FIG. 2) through interior 84 of hub 72, interior 66 of fluid seal 56, interior 94 of needle holder 95, and needle 32 (FIG. 4).

Figure 5:
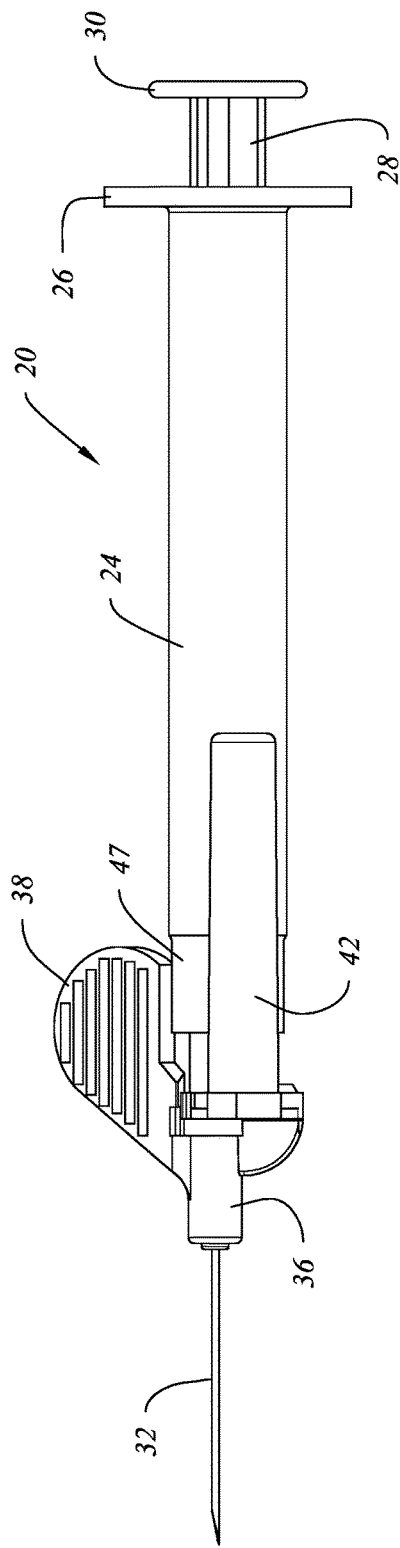
FIG. 5 is a side elevation view of the apparatus of FIG. 1 with the syringe plunger advanced to the post-injection position and the hub assembly rotated clockwise relative to the nose.
Figure 6:
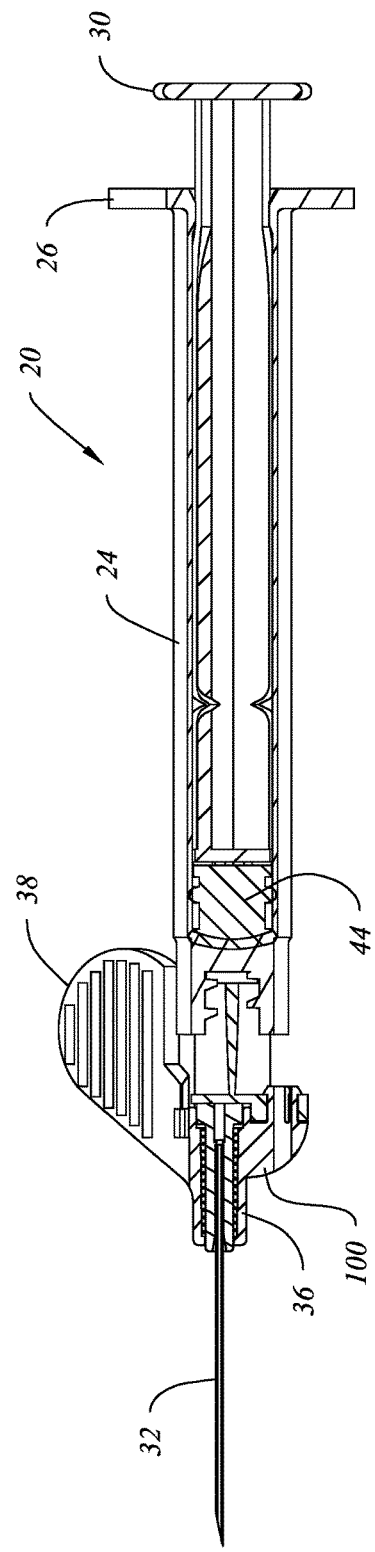
FIG. 6 is a cross-sectional view of the apparatus of FIG. 5 taken along line 6-6 of FIG. 10.

Referring to FIGS. 5 and 6, the assembled combination 20 is again shown, but this time with plunger handle 28 advanced relative to syringe barrel 24 to the point it will be following an injection, when plunger seal 44 has forced the fluid out of fluid chamber 46 as previously shown and described in relation to FIGS. 1 and 2. This is the position in which plunger handle 28 will desirably remain relative to syringe barrel 24 during activation of the retraction mechanism and retraction of needle 32. By comparing the position of retraction tube 42 in FIG. 5 to that shown in FIG. 1, it is apparent that rotation of barrel 24 and retraction tube 42 relative to stabilization tab 38 of nose 35 has already been initiated.

Figure 7:
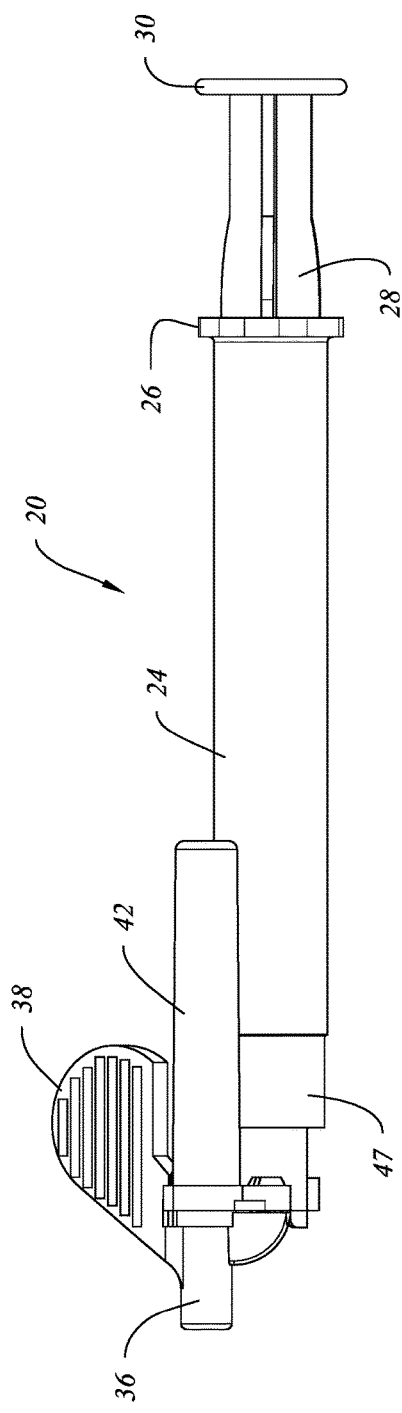
FIG. 7 is a side elevation view of the apparatus of FIG. 5 with the plunger advanced to the post-injection position and the hub assembly rotated further clockwise relative to the nose.
Figure 8:
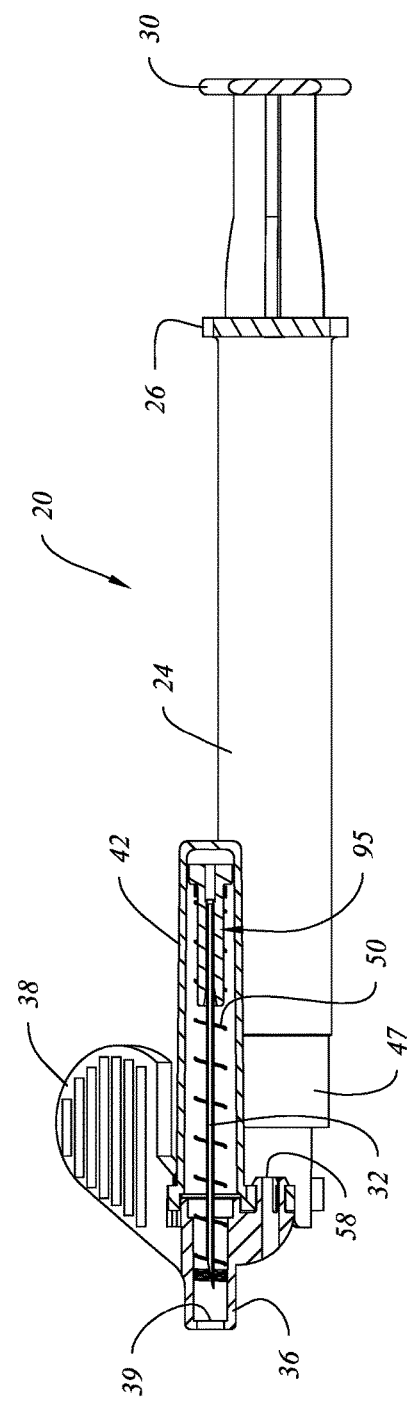
FIG. 8 is a cross-sectional view of the apparatus of FIG. 5 taken along line 6-6 of FIG. 10.

Referring to FIGS. 7 and 8, the assembled combination 20 is again shown, and by comparing the position of retraction tube 42 in FIG. 7 to that shown in FIG. 5, it is apparent that rotation of barrel 24 and retraction tube 42 relative to stabilization tab 38 of nose 35 has continued to a point where retraction has occurred, and retraction spring 50 has propelled needle holder 95 in retraction tube 42 to a position where no portion of needle 32 is exposed forwardly of body 36.

Figure 9:
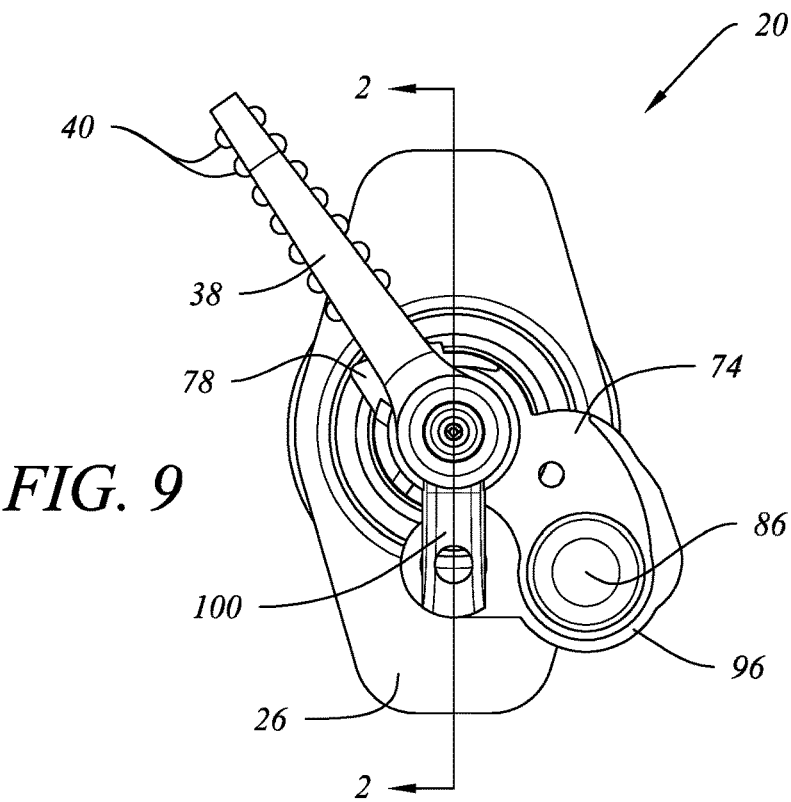
FIG. 9 is a front elevation view of the apparatus of FIG. 1.
Figure 12:
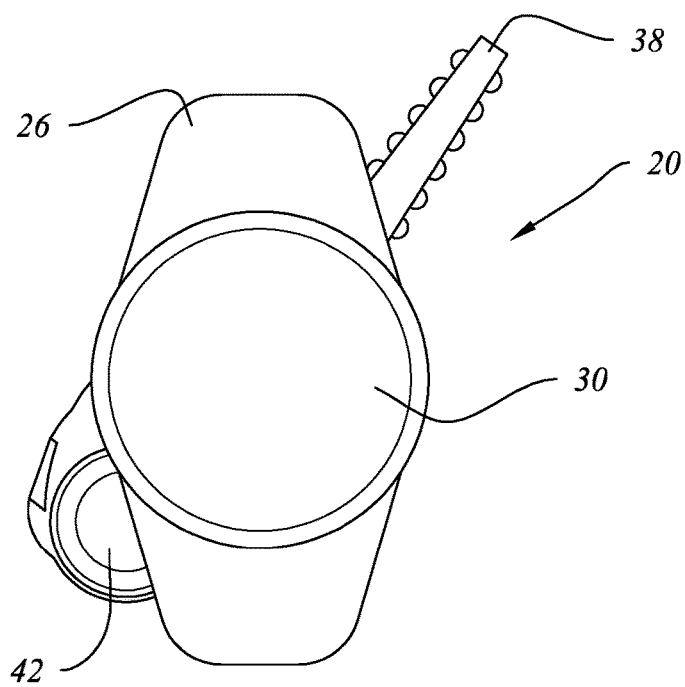
FIG. 12 is a rear elevation view of the apparatus of FIG. 1.

FIG. 9 depicts the relative positions of the components of combination 20 as in FIG. 1, but viewed from the front. FIG. 12 depicts the relative positions of the components of combination 20 as in FIG. 1, but viewed from the rear.

Figure 10:
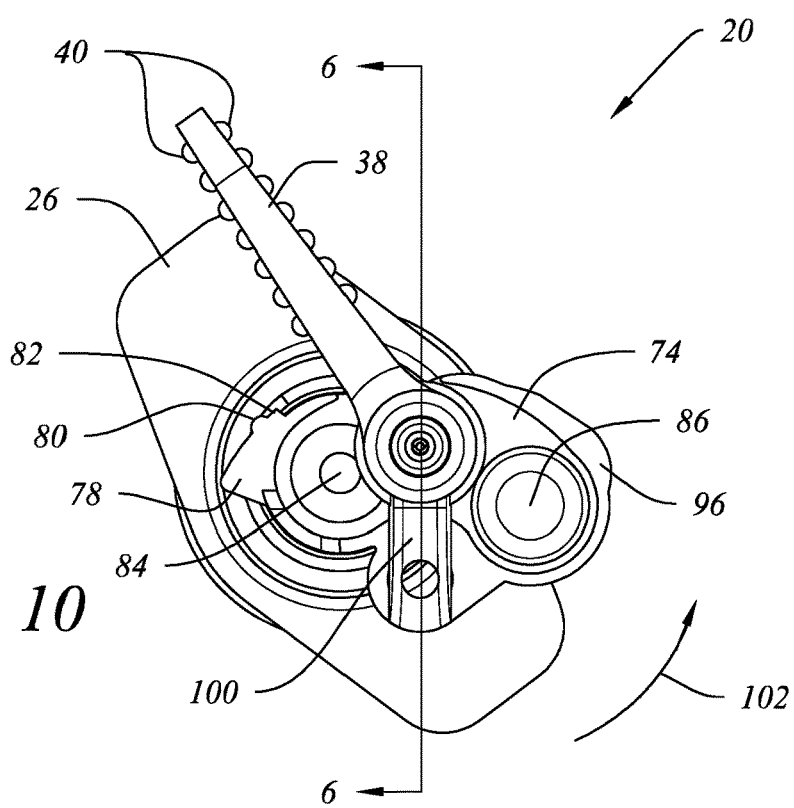
FIG. 10 is a front elevation view of the apparatus of FIG. 5.
Figure 13:
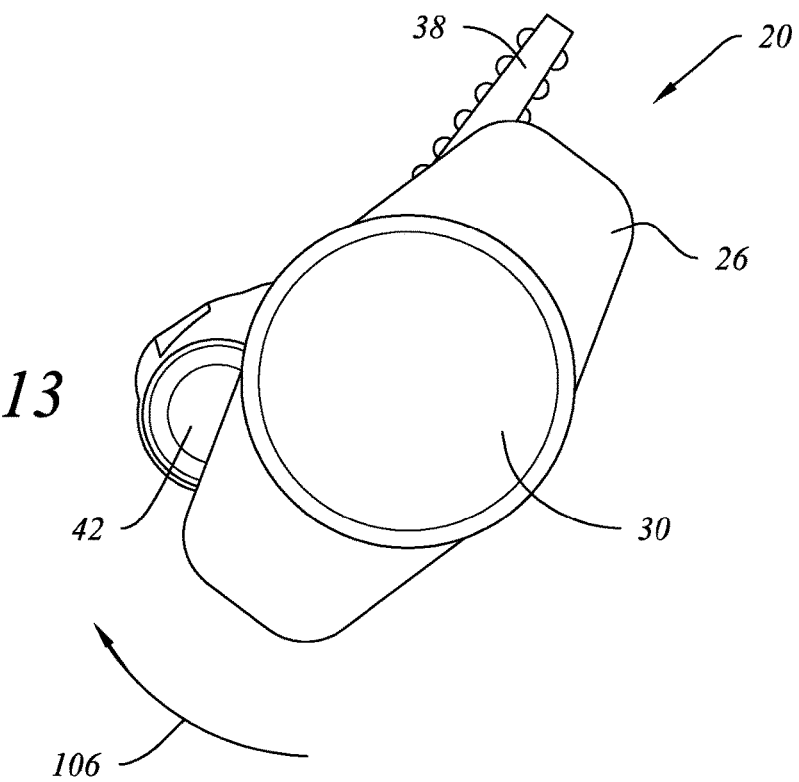
FIG. 13 is a rear elevation view of the apparatus of FIG. 5.

FIG. 10 depicts the relative positions of the components of combination 20 as in FIG. 5, but viewed from the front, with arrow 102 showing the direction of rotation of frame member 74 of hub assembly 48 relative to stabilization tab 38. FIG. 13 depicts the relative positions of the components of combination 20 as in FIG. 5, but viewed from the rear, with arrow 106 showing the direction of rotation of retraction tube 42 and syringe flanges 26 relative to stabilization tab 38.

Figure 11:
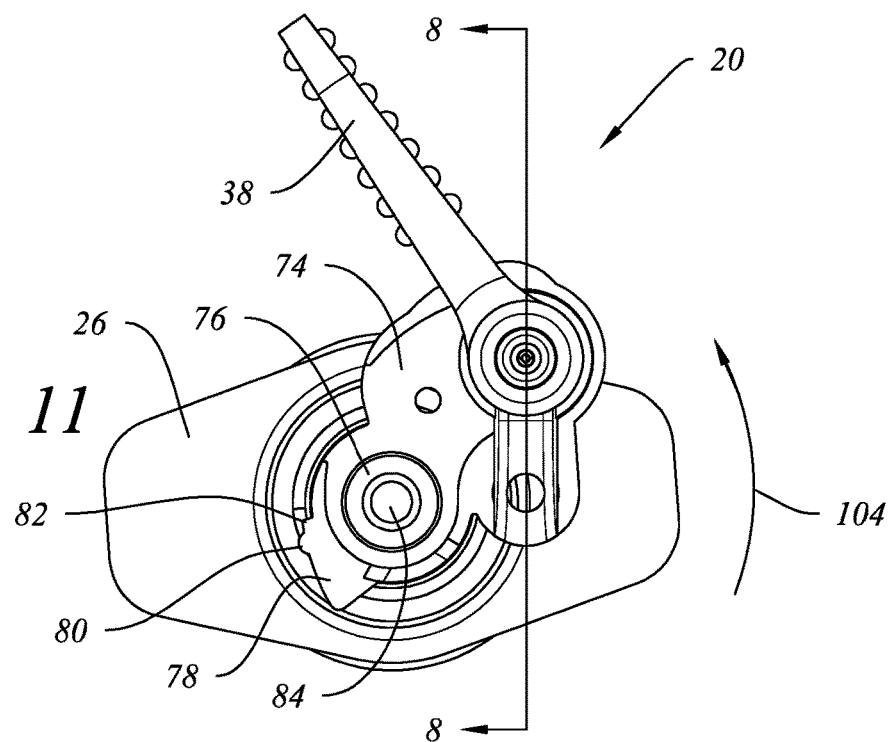
FIG. 11 is a front elevation view of the apparatus of FIG. 7.
Figure 14:
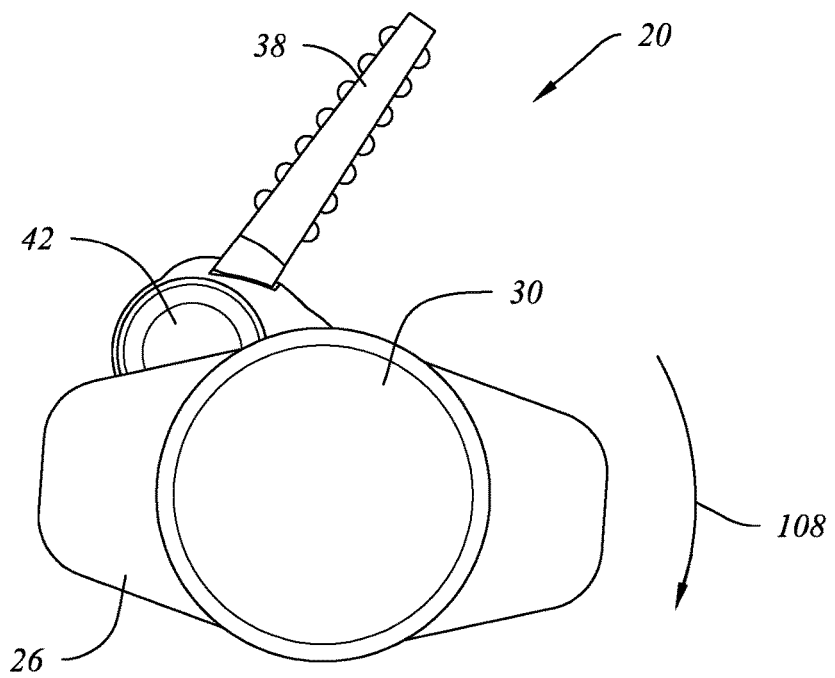
FIG. 14 is a rear elevation view of the apparatus of FIG. 7.

FIG. 11 depicts the relative positions of the components of combination 20 as in FIG. 5, but viewed from the front, with arrow 104 showing the direction of rotation of frame member 74 of hub assembly 48 relative to stabilization tab 38. FIG. 14 depicts the relative positions of the components of combination 20 as in FIG. 5, but viewed from the rear, with arrow 108 showing the direction of rotation of retraction tube 42 and syringe flanges 26 relative to stabilization tab 38.

Figure 17:
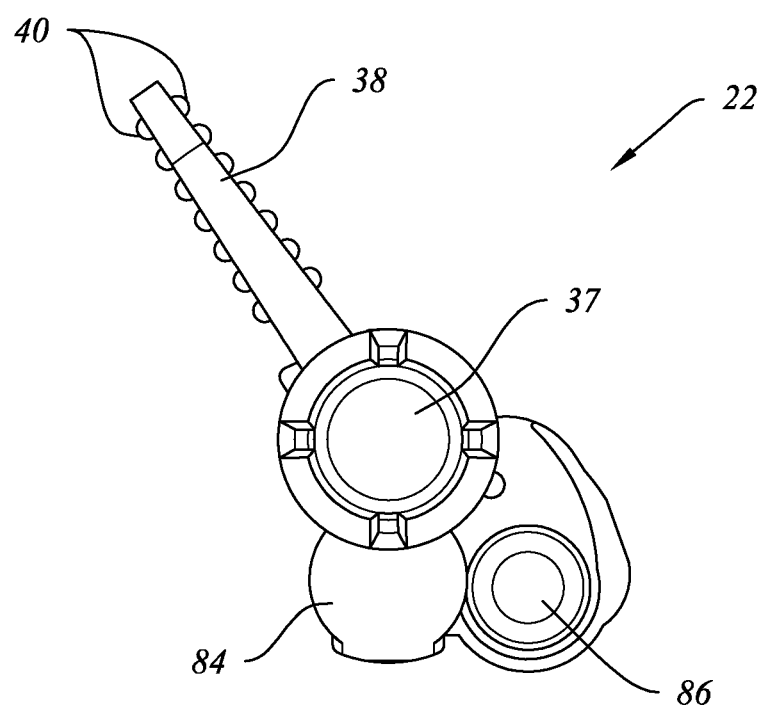

Nose 35, needle holder 95, hub assembly 48, syringe barrel 24 and plunger handle 28 are all desirably moldable from a suitable moldable polymeric material. Such materials and molding methods are believed to be well known to those of ordinary skill in the art. Similarly, it will be appreciated by those of skill in the art of syringe design and manufacture that a medical device such as medical device 22 disclosed here can be used with syringes that are either pre-filled or not, and that may comprise component portions made of glass or other suitable materials for particular applications. Similarly, it will be appreciated that fluid seal 56 and plunger seal 44 are desirably made of a rubbery or elastomeric polymeric material of the types commonly known for use in such medical applications. Similarly, it will be appreciated that materials used in the fabrication of this and other medical devices must be approved by the relevant regulatory authorities for use in such devices. Retraction spring 50 and needle 32 as disclosed are desirably made of stainless steel or any other similarly effective material. A needle cover 37 for medical device 22 is shown in FIGS. 15-17 for use with needle 32 while it is disposed in the forwardly projecting position prior to use, and it will be appreciated by those of skill in the art that such needle covers 37 are needed to protect needle 32 from contamination or damage during shipment and storage, and can be designed and fabricated using known technology.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventors are legally entitled.

We claim:

1. A medical device selectively attachable to a syringe having a barrel with a front end and a back end, a plunger slidably disposed inside the barrel, a fluid chamber disposed forwardly of the plunger, and a plunger handle projecting rearwardly from an opening in the back end of the barrel, the medical device comprising:
   a hub assembly comprising a hub disposed forwardly of the plunger, a retraction tube laterally spaced apart from the hub, and a frame member interconnecting the hub and the retraction tube in substantially fixed, laterally spaced-apart relation to each other;
   a nose projecting forwardly from the hub;
   a rearwardly biased needle retraction mechanism seated inside the nose;
   a retractable needle projecting forwardly of the nose;
   a fluid flow path from the fluid chamber through the hub, nose, needle retraction mechanism and needle;
   wherein the nose is rotatably attached to the hub assembly along an axis of rotation that is parallel to and offset from both a first longitudinal axis through the hub and the retractable needle, and is also parallel to and offset from a second longitudinal axis through the retraction tube.

2. The medical device of claim 1 wherein the hub comprises a rearwardly facing first attachment element that is selectively engageable with a cooperating second attachment element disposed at the front of the barrel.

3. The medical device of claim 2 wherein the first and second attachment elements comprise a luer lock connector.

4. The medical device of claim 3 wherein the first attachment element comprises a plurality of spaced-apart, radially projecting lugs.

5. The medical device of claim 2 wherein the second attachment element comprises at least one female thread disposed inside a collar projecting forwardly from the barrel.

6. The medical device of claim 1 wherein the nose is connected in rotatable relation to the frame member.

7. The medical device of claim 1 wherein a fluid seal is disposed between the nose and the hub.

8. The medical device of claim 7 wherein the fluid seal is seated inside an annular recess in a front face of the hub.

9. The medical device of claim 7 wherein the fluid seal is made of an elastomeric polymeric material.

10. The medical device of claim 1 wherein the needle retraction mechanism comprises a needle holder and a spring.

11. The medical device of claim 10 wherein the needle holder is biased against a fluid seal disposed between the nose and the hub whenever the barrel and hub assembly are coaxially aligned with the retractable needle.

12. The medical device of claim 10 wherein the needle holder is biased against the frame member whenever the needle holder is disposed between the hub and the retraction tube.

13. The medical device of claim 10 wherein the needle holder is aligned with an opening in the front of the retraction tube whenever the retractable needle is retracted.

14. The medical device of claim 10 wherein a portion of the needle holder projects forwardly from the nose prior to needle retraction.

15. The medical device of claim 10 wherein the spring is compressed between an annular surface in the front of the nose and an annular shoulder on the needle holder prior to needle retraction.

16. The medical device of claim 1 wherein the nose further comprises a radially projecting stabilizer tab that is grasped by a user to hold the nose in a substantially fixed position relative to a patient while rotating the barrel and hub assembly from a first position to a second position.

17. The medical device of claim 16 wherein the radially projecting stabilizer tab is textured to render it more graspable by a user.

18. The medical device of claim 1 wherein the nose and hub assembly are each made of moldable polymeric material.

19. The medical device of claim 1 configured for use with a syringe having a glass barrel.

20. The medical device of claim 1 configured for use with a syringe having a syringe barrel molded from a suitable moldable polymeric material.

21. The medical device of claim 1 configured for use with a prefilled syringe.

22. The medical device of claim 1 wherein the hub, retraction tube and frame member are molded from a suitable moldable polymeric material.

23. The medical device of claim 1 wherein the needle retraction mechanism provides a retraction force upon activation that is sufficient to retract the needle directly from a patient into which the needle is inserted during an injection.

24. The medical device of claim 1 in combination with a syringe attached to the hub assembly.

25. A medical device comprising in combination:
   a hub assembly comprising a retraction tube, a hub, and a frame member connecting the retraction tube and hub, wherein the hub is selectively attachable to the front of a syringe barrel having a fluid chamber disposed inside the barrel and a plunger slidably engaging an inside wall of the barrel;
   a nose attached to the hub assembly so that the hub assembly is rotatable in at least one direction through a defined arc relative to the nose;
   a needle retraction mechanism seated inside the nose; and
   a needle projecting forwardly of the nose;
   wherein the needle is selectively retractable into the retraction tube by rotating the syringe and hub assembly relative to the nose about a longitudinal axis that is parallel to and offset from a longitudinal axis through the needle and a longitudinal axis through the retraction tube.

26. The medical device of claim 25 wherein the hub assembly comprises a hub providing fluid communication between the fluid chamber and the nose.

27. The medical device of claim 26 comprising a fluid seal disposed between the hub and the nose.

28. The medical device of claim 25 wherein the retraction tube is laterally spaced-apart from the hub.

29. The medical device of claim 25 wherein the frame member connects the hub and the retraction tube in substantially fixed relation to each other.

30. The medical device of claim 25 wherein the hub assembly is rotatable in only one direction relative to the nose immediately following an injection.

31. The medical device of claim 25 wherein the needle retraction mechanism provides a retraction force upon activation that is sufficient to retract the needle directly from a patient into which the needle is inserted during an injection.

32. The medical device of claim 25 in combination with a syringe attached to the hub assembly.

33. The medical device of claim 26 further comprising a fluid flow path extending from the fluid chamber to the needle.

* * * * *